United States Patent [19]

Woodson, III

[11] Patent Number: 5,709,216

[45] Date of Patent: Jan. 20, 1998

[54] DATA REDUCTION OF SENSED VALUES IN AN IMPLANTABLE MEDICAL DEVICE THROUGH THE USE OF A VARIABLE RESOLUTION TECHNIQUE

[75] Inventor: Drury L. Woodson, III, Alvin, Tex.

[73] Assignee: Sulzer Intermedics, Inc., Angleton, Tex.

[21] Appl. No.: 478,473

[22] Filed: Jun. 7, 1995

[51] Int. Cl.$^6$ ........................................... A61B 5/04
[52] U.S. Cl. .................. 128/710; 128/673; 128/736; 128/637
[58] Field of Search .................... 128/695 R, 696, 128/706, 710, 711, 637, 673, 736; 364/413.02, 413.03, 413.04, 413.05, 413.06; 607/19-23, 59; 382/128, 232, 239, 244, 246

[56] References Cited

U.S. PATENT DOCUMENTS

| | | | |
|---|---|---|---|
| 4,449,536 | 5/1984 | Weaver | 128/696 |
| 4,567,883 | 2/1986 | Langer et al. | 128/696 |
| 4,716,903 | 1/1988 | Hansen et al. | 128/696 X |
| 4,947,858 | 8/1990 | Smith | 128/696 |
| 5,263,486 | 11/1993 | Jeffreys | 128/696 |
| 5,354,315 | 10/1994 | Armstrong | 607/4 |
| 5,398,183 | 3/1995 | Elliott | 364/413.06 |

FOREIGN PATENT DOCUMENTS 0691620  1/1966  European Pat. Off. ........ G06F 19/00

OTHER PUBLICATIONS

Passariello, G., et al., "Arithmetic Coding for EDG Data Compression," Proceedings of the Computers in Cardiology Meeting, Sep. 23–26, 1991, Venice Italy, *Institute of Electrical and Electronics Engineers*, 1992 IEEE p. 593–596.
Tai, S.C., "SLOPE—a Real–time ECG Data Compressor," *Medical & Biological Engineering & Computing*, vol. 29, No. 2, Mar. 1, 1991, pp. 175–179.

Jun., L., "Full Use of Memory for 12bit ADC Data Acquisition," *Electronic Engineering*, vol. 63, No. 780, Dec. 1, 1991, p. 30.

Hsia, P–W, et al., "An Automated System for ST Segment and Arrhythmia Analysis in Exercise Radionuclide Ventriculography," *IEEE Transactions on Biomedical Engineering*, New York, NY, vol. BME–33, No. 6 (Jun. 1986), pp. 585–593.

Jenkins, J., et al., "Automated Arrhythmia Analysis Combined with ST Analysis for Exercise Monitoring," Proceedings of Computers in Cardiology, Sep. 8–11, 1985, Linkoping, Sweden, 1985 *IEEE*, IEEE Computer Society Press, New York, NY, pp. 229–232.

Dotsynsky, I.A., et al., "A Digital Heart–Ratemeter Using an E.P.R.O.M. Converter," *Medical & Biological Engineering & Computing*, vol. 18, No. 4 Jul. 1980, Stevenage, G.B., pp. 481–482.

*Primary Examiner*—Jeffrey R. Jastrzab
*Attorney, Agent, or Firm*—Conley, Rose, & Tayon, PC; Michael F. Heim

[57] ABSTRACT

An implantable device which acquires physiological data and status information. The physiological data is compressed, reducing the memory requirement of the implantable device and/or increasing the amount of data that can be stored. The compression technique uses variable resolution while maintaining desired accuracy. The physiological data, such as heart beat interval time, is converted into a digital value. The digital representation then is divided into sub-ranges, and various resolution values are assigned to each sub-range. Each resolution is selected to stay within the desired accuracy. The interval time is divided by the particular resolution to obtain a digital value for the interval time within that range. The digital value then is corrected based upon the sub-range to obtain the compressed encoded digital value, which can then be stored in memory together with other desired data.

44 Claims, 4 Drawing Sheets

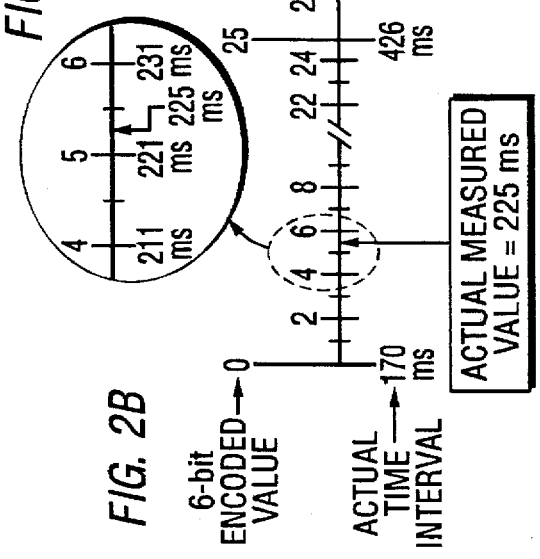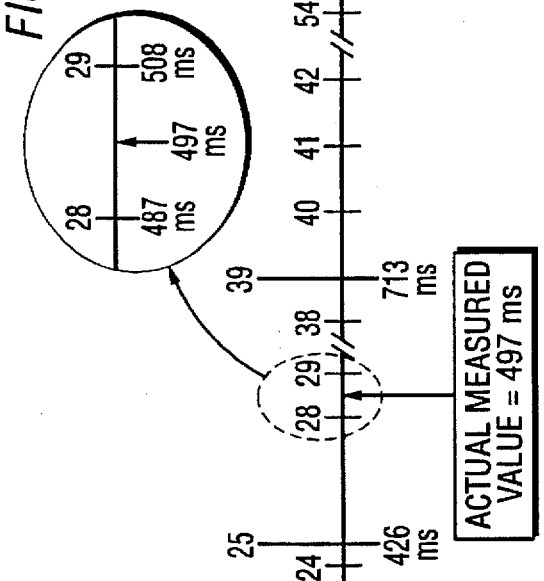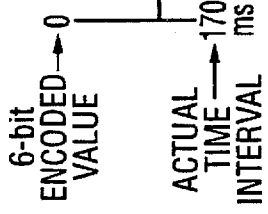

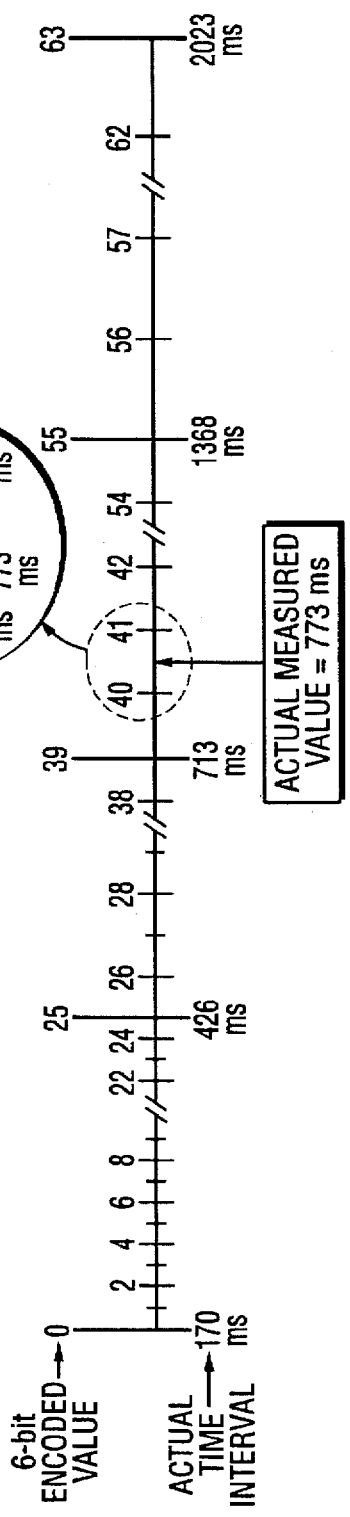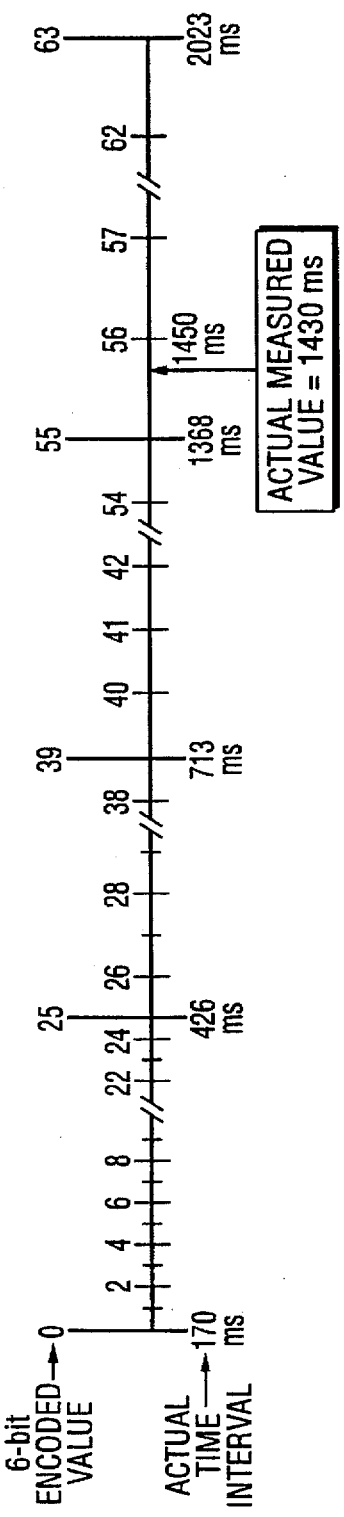

DATA REDUCTION OF SENSED VALUES IN AN IMPLANTABLE MEDICAL DEVICE THROUGH THE USE OF A VARIABLE RESOLUTION TECHNIQUE

BACKGROUND OF THE INVENTION

The present invention generally relates to implantable medical devices and the storage of sensed waveforms in memory. More particularly, the present invention relates to implantable devices that employ data compression techniques during data storage. Still more particularly, the present invention relates to implantable devices that sense physiological values, convert those values to digital signals, and compress the digital representations of the sensed physiological data using variable resolution techniques.

It is often desirable to embed an implantable device in a patient to monitor one or more physiological parameters such as heart rate, temperature, oxygen saturation level, and blood pressure during normal day-to-day activities of the patient. Sensors attached to, or internal to, the implantable device are capable of providing indications of how the physiological parameters vary over time. The sensor typically provides an output signal that comprises an analog signal. To be stored, the analog signal must be converted into a standard-sized digital signal. Once digitized, the physiological data signals usually are stored in the implanted device's memory and downloaded at a later time for observation by a care provider. The treatment of the patient may depend on the medical inferences drawn from the physiological data stored in the implanted device.

Because of size and power consumption constraints in the implantable medical device, the on-board memory in an implantable device is capable of storing only a fraction of the available data. To maximize the quantity of data that can be stored, it is advantageous if each digitized signal can be represented with a minimum number of bits. Various data compression techniques have been employed to reduce the number of bits required to store a desired set of data. For example, U.S. Pat. No. 5,354,315 discloses an algorithm for compressing an electrocardiogram wave form. The cardiac wave form is sampled and digitized and the set of digitized values are compressed by measuring the difference in amplitude between successive cardiac cycles (i.e., heartbeats). This technique takes advantage of the fact that the difference between one cardiac cycle and the following cycle statistically is small. Although this method may work well for electrocardiograms, it may not work at all for reduction of other types of physiological data. Compression techniques are generally known and commonly used for data storage. These conventional techniques, however, are not generally designed for critical physiological parameters. In particular, certain measured parameters may require a high degree of resolution, while others do not. Thus, general compression techniques typically do not address the particular resolution problems encountered in data compression of physiological parameters.

Often it is desirable to monitor several physiological parameters such as heart rate, temperature, and body activity level over a long period of time. Similarly, it may be desired to sense various parameters associated with a single organ. For example, a cardiac pacemaker may include sensing functions to obtain data on the atrial pacing ram, the ventricular pacing rate, or physical exertion measurements of the patient. Because these parameters may vary considerably with respect to rime, numerous values must be acquired over a period of rime. A health care provider also may need to know some aspect of the patient's physical exertion status for each acquired and stored physiological datum. This status information, taken together with the heart rate, might reflect normal or anomalous behavior of the heart. The status information may identify other information such as general condition of the body or time of day (e.g., day or night). It would be advantageous if a compression technique could be developed to minimize the number of bits required for the sensed parameters to permit the encoding of other information with a particular sensed value. It would also be advantageous to develop a compression technique which provides increased resolution where necessary to eliminate error, especially in highly critical sensed values.

SUMMARY

The present invention solves the shortcomings and deficiencies of the prior art by constructing an implantable medical device capable of processing and compressing physiological data and status information. In the preferred embodiment, compressed data requires no more than six bits of memory storage, permitting two bits to be used to identify status information, such as the particular type of sensing that is being performed. The compression technique employs variable resolution on sensed parameters to minimize the potential error to less than 6%. In one exemplary embodiment, the physiological data comprises heart rate values estimated from the time interval between heart beats. The time interval values, which typically lie in the approximate range of 170 ms to 2000 ms (representing 1830 data points), are converted to 6-bit values during compression. The compression technique takes advantage of the fact that less resolution is needed at slower heart rates to provide more resolution at higher heart rates.

According to the preferred embodiment, the available time interval range is separated into a plurality of sub-ranges with each sub-range having a different resolution. Compression is accomplished by ascertaining which sub-range a time interval value falls in and applying the appropriate resolution for that interval to obtain an appropriate 6-bit encoded digital code.

BRIEF DESCRIPTION OF THE DRAWINGS

Other objects and advantages of the invention will become apparent upon reading the following detailed description and upon reference to the accompanying drawings in which:

FIGS. 2A–2E are exemplary interval graphs which illustrate the conversion process between actual inter-heartbeat interval times to compressed digital data values.

FIG. 2F is an enlarged view of a portion of the interval graph of FIG. 2B.

FIG. 2G is an enlarged view of a portion of the interval graph of FIG. 2C.

FIG. 2H is an enlarged view of a portion of the interval graph of FIG. 2D.

Figure 1:
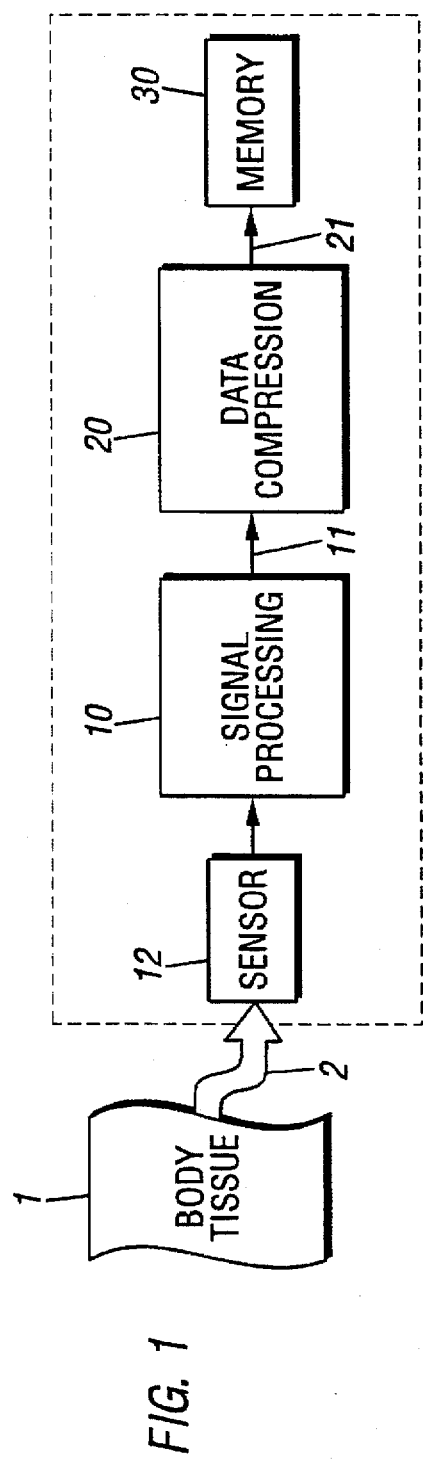
FIG. 1 is a schematic block diagram of an implantable device capable of data compression.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENT

Referring now to FIG. 1, an implantable medical device 3 capable of variable resolution data reduction functionally comprises signal processing device 10, data compression logic 20, and memory 30. The signal processing device 10 preferably provides amplification, filtering, timers, analog-to-digital conversion, input/output interfaces, and general control features. This type of device is well known in the art and forms the "core" of most implantable devices. A physiological signal 2 generated by body tissue 1 is coupled to the signal processing device 10. The signal processing device 10 includes one or more sensors 12 for detecting physiological activity and producing a digital output signal on line 11. The signal processing device 10 also preferably includes, amplifiers and filters for conditioning the analog signal, and an analog-to-digital converter to digitally encode the analog signal. In accordance with the preferred embodiment, the digital signal is compressed in data compression device 20, and transmitted to memory array 30 on output line 21, where the compressed digital code is stored. The memory array 30 preferably is comprised of random access memory (RAM) chips. In the preferred embodiment, the body tissue 1 may comprise, for example, the human heart, and the physiological signal 2 may include the electrical activity of the heart. The electrical activity of the heart preferably is coupled to the signal processing device 10 via electrodes (not shown specifically). In other embodiments, the physiological signal 2 may include temperature, oxygen saturation level, blood pressure, body activity level, and other parameters.

For certain physiological parameters the implantable device may generate an electrical signal indicative of that parameter without a physical connection to the body tissue 1. For example, pulse oximetry sensors may be located inside the housing (or can) of the implantable device. Optical energy generated by the pulse oximeter reflects off body tissue such as blood and the reflected signal is collected by the sensor. By comparing the generated signal with the reflected signal, a measure of the blood's oxygen saturation level may be developed. Also, accelerometers may be incorporated into implantable devices. Accelerometers typically are sensitive to changes in body motion in various directions and may provide useful information to a health care provider regarding physical exertion levels of the patient.

If electrical activity data of the heart is collected, the signal processing device 10 will process those signals to provide an estimate of heart rate or the number of times the heart beats each minute. Typically, an estimate of heart rate is inferred by measuring the interval time (or interval period) between cardiac cycles, which is the commonly known electrocardiogram for each heart beat. Frequency is inversely proportional to period. Thus, by measuring the period t of the electrocardiogram, the frequency f or heart rate can be inferred by inverting the period values (f=1/t). For example, if the time period between two heart beats is 1 second, heart rate is estimated by computing the value 1 beat/1 sec. Converting from seconds to minutes, which is the conventional unit for heart rate, provides (1 beat/1 sec)(60 sec/1 min) or 60 beats per minute (BPM).

The signal processing device 10 measures the time t between pairs of successive heart beats. To avoid up-front processing, the time interval between beats (or average time interval between beats in a sampling period) is stored in memory 30. By subsequently inverting these encoded values when they are retrieved from memory 30, a set of heart rate values is obtained, each value representing the heart rate at a specific moment in time. Heart beat intervals may be sampled by the signal processing device 10 periodically. If, for example, the heart beat intervals are sampled once every nine minutes for a sampling period of one minute, then six minutes of heart beat intervals are stored every hour. If the heart beat rate is 100 BPM, then approximately 100 interval values may be stored each minute. Thus, with this sampling rate, 600 digital signals would be encoded each hour. If the encoded digital signal requires 16 bits (or 2 bytes), then 1200 bytes of storage are used each hour. At this sampling rate, 833 hours (approximately 1 month) of samples can be stored in 1 Megabyte of memory. If that same data could be compressed to an 8 bit (or 1 byte) signal, then approximately 1650 hours (approximately 2 months) of sampling could be stored in that same 1 Megabyte of memory. While the quantity of memory consumed can be conserved by averaging heart rate values during a sampling period, the problem with memory space limitations remains. The advantages of data compression for digital values is desirable especially in light of the limited amount of memory available in an implantable medical device.

In accordance with the preferred embodiment of the present invention, the set of inter-heart beat time intervals measured by the signal processing capability, therefore, is relayed to the data compression capability 20. Expected heart beat rates may range from 30 BPM to 353 BPM. Time intervals for this range fall within the approximate range of 170 milliseconds (ms) to 2000 milliseconds. Thus, approximately 1830 different interval values (in milliseconds) exist in the expected range. Encoding 1830 values requires 11 bits ($2^{11}$=2048). Thus, some type of compression is desired so that the measured interval values can be stored in 8 bits (1 byte) or less, without introducing excessive error. To insure an error of less than 6%, for this range, 10.24 millisecond resolution is used to digitally encode the time interval. With 10.24 ms resolution, 179 time interval values exist in the anticipated range. As such, eight bits are needed to store these data ($2^8$=256), if a resolution of 10.24 is desired.

Furthermore, along with each time interval, status information must be stored in the memory 30 to indicate the type of sensing that is being conducted. Measuring the inter-heart beat time periods may happen during certain physiological conditions monitored by the implantable device. A health care provider generally needs to be aware of these physiological conditions when viewing the heart rate data. Some of the relevant physiological conditions the status information may include are identification of premature ventricular event, atrial pacing, atrial sense ventricular pace, or physical exertion. Preferably, at least two bits of status are stored with each time interval providing four unique status identifiers.

Ten bits of data, therefore, are required to store the eight-bit time interval values and associated two-bit status identifier. Memory specifications may force the use of two bytes to store each set of data (i.e., one time interval and one status identifier) because memory typically is partitioned in byte (8 bit) segments. The present invention compresses the data so that only six bits are needed to store the interval values, instead of eight. Each set of data can then be stored in one byte of memory, thereby reducing the total memory requirement for the implantable device by half. In accordance with the preferred embodiment of this invention, the data compression device 20 reduces the data with a sufficient resolution to maintain a required accuracy without effecting the quality of the health care.

The present invention stores inter-heart beat time periods and indications of a physiological condition with only 8 bits of memory while maintaining a resolution with less than 6% error. Preferably 2 bits are dedicated to encoding four possible physiological condition events and 6 bits are dedicated to encoding the measured parameter such as time interval, accelerometer value, and temperature. These six bits provide 64 different binary values ($2^6=64$). The following description focuses on the method for associating each time interval value with one of 64 different binary values, with the understanding that the same principles may be applied to compress other signals.

In accordance with the preferred embodiment of the present invention, the data reduction technique uses tighter resolutions at the smaller heart beat interval values (which correspond to higher heart beat rates) and relatively looser resolutions for the larger heart beat interval values. If the desired accuracy of the reported heart rate is ±1 BPM, this corresponds to an interval resolution of ±1.8 ms at 180 BPM and 64.5 ms at 30 BPM. Thus, the higher the heart beat rate (and therefore the smaller the interval between heart beats), the more critical the resolution becomes. In recognition of this concept, the present invention provides different resolutions for heart beat intervals by dividing the expected heart beat interval range into two or more sub-ranges, with different resolutions for encoding heart beat interval values for each of the sub-ranges. Consequently, the 64 encoded values that are available with six bits are not distributed uniformly throughout the entire expected heart beat interval range of approximately 170 to 2000 ms. Rather, subsets of the 64 total time steps are distributed uniformly in a plurality of sub-ranges, with resolution values differing between sub-ranges. This technique allows for some combination of either (1) reducing the storage requirements of the data or (2) selectively increasing resolution across portions of the input range.

Figure 2A:
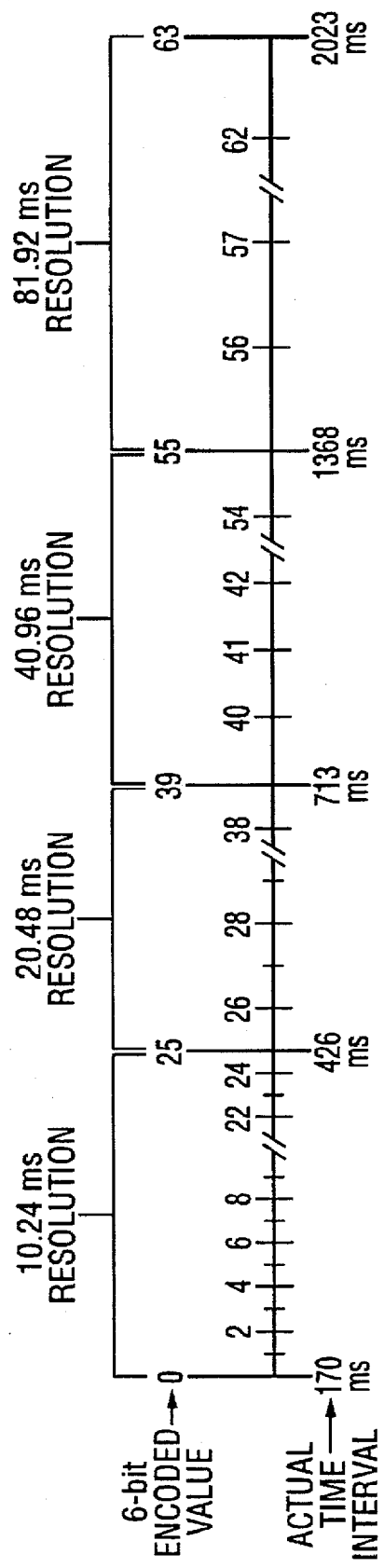

FIG. 2A depicts an exemplary breakdown of the possible heart beat intervals (170 ms–2023 ms) into the 64 encoded values available with six bits of memory. The values on the line indicate the value of the binary encoded signal (0–63). Thus, the value of "25" would be encoded as (011001). The values below the time interval line indicate the range of actual time interval values from 170 ms to 2023 ms separated into four exemplary sub-ranges: 170 ms to 426 ms, 427 ms to 713 ms, 714 ms to 1368 ms, and 1369 ms to 2023 ms. The resolution provided by the present invention differs between sub-ranges. In the 170 ms to 426 ms range, a 10.24 ms resolution preferably is provided. In the 427 ms to 713 ms range, a resolution of 20.48 ms is preferably provided for each encoded value. In the 714 ms to 1368 ms range, a 40.96 ms resolution preferably is provided. Finally, in the 1369 ms to 2023 ms range, a resolution of 81.92 ms is provided. The resolution of 10.24 ms in the first sub-range defines 26 time steps (0 through 25) in that sub-range, requiring 26 of the 64 available values to encode. A resolution of 20.48 ms in the second sub-range provides 14 (26 through 39) time steps in that sub-range requiring 14 of the 64 available values to encode. A resolution of 40.96 ms in the third sub-range provides 16 time steps (40 through 55) in that sub-range requiring 16 of the 64 available values to encode. A resolution of 81.92 ms in that fourth sub-range provides 8 time steps (56 through 63) in that sub-range requiring 8 of the 64 available values to encode. With this variable resolution capability, the actual time intervals between heart beats can be digitally encoded into incremental steps between 0 and 63, with less than a 6% error for each encoded value.

Once the time interval between successive heart beats is measured, that value is converted to a 6-bit time step value that is stored in the implantable device's memory 30. The following four examples describe the preferred conversion process, with the understanding that more or less sub-ranges could be provided, as desired.

The first example is shown in FIG. 2B, in which the actual measured time interval is 225 ms, as indicated by the arrow below the time interval line. As shown in the blown-up section (FIG. 2F) of the time interval line, the 225 ms time interval lies between the marks for 221 ms and 231 ms which correspond to encoded values 5 and 6, respectively. The reduction algorithm encodes the 225 ms interval as "5" because the 225 ms measured interval, as shown, is closer to time step 5 than 6. Accordingly, a binary "5" (000101) will be stored in memory 30 in the six available bits. The other two bits representing status information are combined with the six encoded bits for heart beat interval to produce the byte of encoded information to be stored.

The second example, shown in FIG. 2C, demonstrates the reduction process for an actual time interval falling within the interval range of 426 ms to 713 ms. The actual measured time interval from signal processing device 10 (FIG. 1) is 497 ms, as indicated by the arrow below the lime interval line. As shown in the blown-up section (FIG. 2G) of the time interval line, the 497 ms time interval lies between the marks for 487 ms and 508 ms which correspond to encoded values 28 and 29, respectively. The reduction algorithm encodes the 497 ms interval as "28" because the 497 ms actual interval is closer to time step 28 than 29. Accordingly, a binary "28" (011100) will be stored in memory 30 in the six available bits for heart beat interval periods.

The third example, shown in FIG. 2D, demonstrates the reduction process for an actual time interval falling within the interval range of 713 ms to 1368 ms. The actual measured time interval in this example is 773 ms, as indicated by the arrow below the time interval line. As shown in the blown-up section (FIG. 2H) of the time interval line, the 773 ms time interval lies between the marks for 754 ms and 795 ms which correspond to encoded values 40 and 41, respectively. The reduction algorithm will encode the 773 ms interval as "40" because the 773 ms actual interval, as shown, is closer to time step 40 than 41. Accordingly, a binary "40" (101000) will be stored in memory 30 in the six bits available for storage of heart beat interval periods.

The fourth example, shown in FIG. 2E, demonstrates the reduction process for an actual time interval falling within the interval range of 1368 ms to 2023 ms. The actual measured time interval in the example of FIG. 2E is 1430 ms, as indicated by the arrow below the time interval line. As shown on the time interval line, the 1430 ms actual time interval lies between the marks for 1368 ms and 1450 ms which correspond to encoded values 55 and 56, respectively. The reduction algorithm will encode the 1430 ms interval as "56" because the 1430 ms actual interval, as shown, is closer to time step 56 than 55. Accordingly, a binary "56" (111000) will be stored in memory 30.

Figure 3:
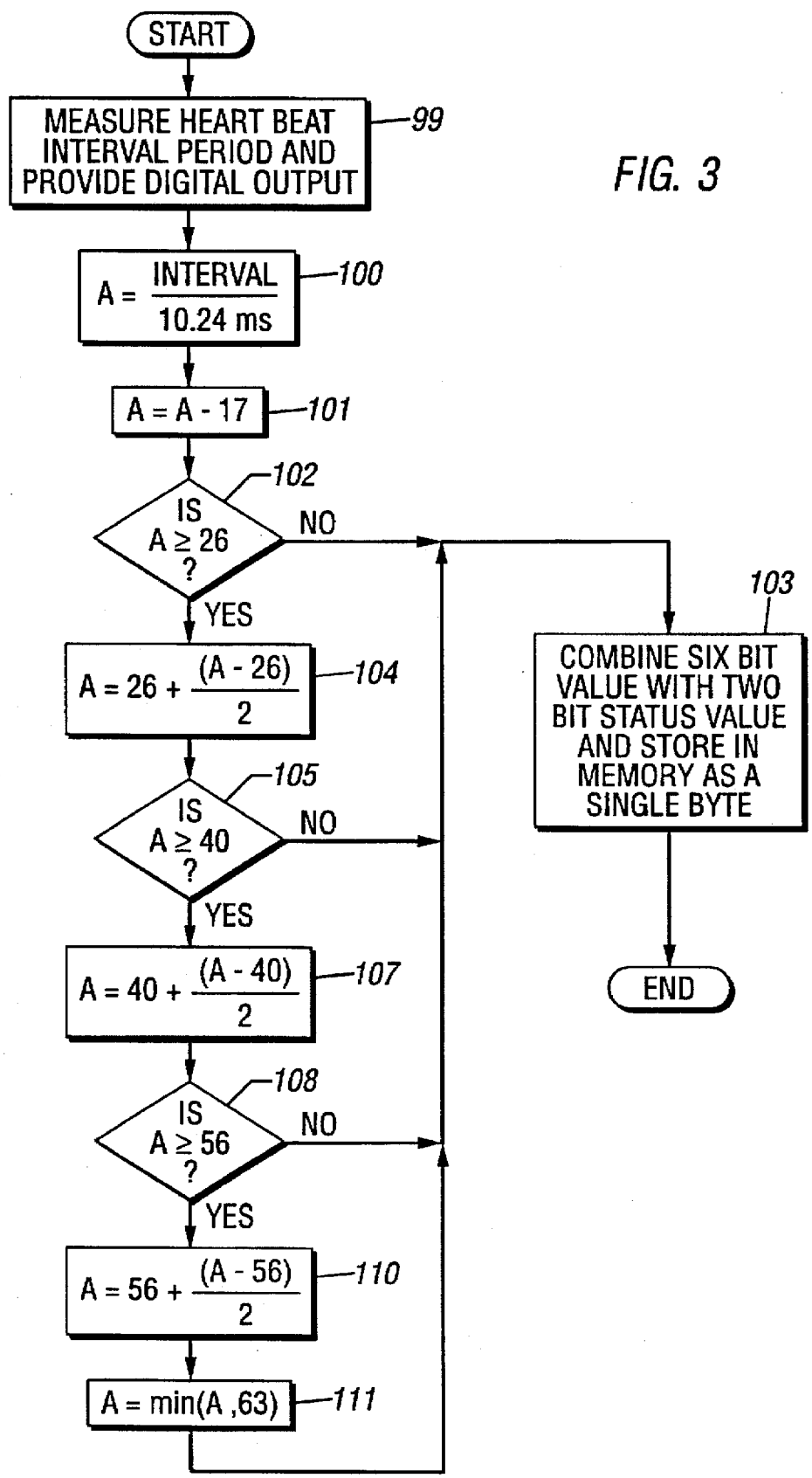
FIG. 3 is a flow chart illustrating the exemplary compression technique for converting heart beat interval times to compressed digital values.

Referring now to FIGS. 1, 2A and 3, an exemplary process for converting the actual measured time intervals from signal processing device 10 into 6-bit encoded values for storage in memory 30 will now be described. The variable A identifies the 6-bit encoded value and lies within the range of 0 to 63. Initially, in step 99, the signal processing device 10 obtains a measurement of the time interval between heart beats and provides a digital signal indication of the measured heart beat interval value (shown as the variable INTERVAL in FIG. 3). In step 100, A is first estimated by dividing the actual heart beat interval value (INTERVAL) by 10.24 ms, which is the resolution for the interval range of 170 ms to 426 ms. The expected range for the heart beat interval values (INTERVAL) is approximately 170 ms to 2023 ms, representing heart rates from 30 BPM to 353 BPM. Because the minimum interval value expected is 170 ms, 17 is subtracted from A in step 101, representing the approximately 17 time steps between 0 and 170 ms with 10.24 ms resolution. Accordingly, the time step 0 corresponds to a measured heart beat interval value of 170 ms (and below), and thus encoded values 0 through 17 are not wasted by assigning them to heart beat intervals unlikely ever to occur.

A comparison between the value A and the value "26" is performed in step 102 which identifies if the measured heart beat interval lies within the range of 170 ms to 426 ms. If so, the encoding routine branches to step 103 because A, as calculated, represents the correct time step value to be stored in the implantable device's memory 30 and no further processing is required. If A is found to be greater than or equal to 26 in step 102, then further action must be taken because the actual heart beat interval value lies within a range that has a resolution different than the 10.24 ms resolution of the first range.

Assuming the time interval lies within the second range, 427 ms to 713 ms, correction must be made for the fact that the resolution changes to 20.48 ms in this range. The correction is performed for A in step 104 as follows:

$$A = 26 + \frac{(A-26)}{2}.$$

In step 105, A is compared to the value 40 to determine if the measured heart beat interval is greater than 713 ms, in which case further correction is needed to compensate for further changes in resolution for other ranges (714 ms to 1368 ms, or 1369 ms to 2023 ms). If A is less than 40, the algorithm branches to step 103.

In step 107, a correction is performed to compensate for the resolution of the 714 ms to 1368 ms range. Thus, in step 107, A is modified as follows:

$$A = 40 + \frac{(A-40)}{2}.$$

If the heart beat interval falls outside the range of 714 ms to 1368 ms (and thus is in the range 1369 ms to 2023 ms), as determined by comparing A to the value 56 in step 108, one final correction is performed for A in step 110 as follows:

$$A = 56 + \frac{(A-56)}{2}.$$

If the value for A is found to be less than 56 in step 108, the algorithm branches to step 103. If not, the value for A is checked in step 111 to make sure that it is not greater than 63, (i.e., a time interval greater than 2023 ms) which would require more than 6 bits to encode. If A is greater than 63, it is set equal to 63.

As an alternative to the method shown in FIG. 3, the measured heart beat interval value may be sequentially compared with the upper and lower interval values in each sub-range to determine which sub-range the measured heart beat interval value falls within. The lower interval value for that sub-range then is subtracted from the measured heart beat value to obtain a difference. This difference then is divided by the resolution value for that sub-range to obtain a relative encoded value. The starting encoded value for the range then is added to the relative encoded value to obtain the correct digital encoded value. Thus, for example, and referring to FIG. 2A, if the measured heart beat interval was 500, then an initial comparison with the sub-range heart beat interval values (170 ms and 426 ms; 427 ms and 713 ms; 714 ms and 1368 ms; and 1368 ms and 2023 ms) would indicate the measured interval fell within sub-range number 2. The start interval value, 426 ms would be subtracted from the measured value to obtain a difference of 74 ms. This value then is divided by 20.24, the resolution for sub-range number 2. This provides a quotient of approximately 4. The start encoding value for sub-range number 2 (which is 25) is added to 4 to get a digital encoded value of 29 (or a 6-bit binary 011101). This value is stored in memory together with the 2-bit status information.

The numerical values contained herein merely characterize the present invention's preferred embodiment and are not intended to limit the scope of the invention. Numerous variations and modifications will become apparent to those skilled in the art once the above disclosure is fully appreciated. It is intended that the following claims be interpreted to embrace all such variations and modifications.

What is claimed is:

1. An implantable medical device for sensing a physiological parameter and generating status information, said implantable medical device storing encoded signals indicative of the sensed physiological parameter and said status information, comprising:

a sensor for sensing the physiological parameter and providing an output signal indicative of said physiological parameter;

a signal processing device for generating status information, said signal processing device also receiving the output signal from said sensor and providing a digital signal representing the sensed physiological parameter;

a data compression device for compressing the digital signal into a digital encoded signal with a predetermined bit width n, wherein the data compression device divides the digital signal from said signal processing device into a plurality of sub-ranges, and applies a different resolution value to each sub-range during compression; and a memory device for storing said digital encoded signal, together with said status information, in a location in memory with a bit width x.

2. An implantable device as in claim 1, wherein said digital signal includes a bit width greater than n.

3. An implantable medical device as in claim 1, wherein the bit width n of the digital encoded signal is less than or equal to eight.

4. An implantable medical device as in claim 3, wherein the bit width n of the digital encoded is less than or equal to six.

5. An implantable medical device as in claim 1, wherein the output signal from said signal processing device provides an indication of time interval between heart beats.

6. An implantable medical device as in claim 5, wherein said time interval between heart beats is within an expected lower and upper interval value.

7. An implantable medical device as in claim 6, wherein the expected lower and upper values are approximately 170 milliseconds and 2000 milliseconds, respectively.

8. An implantable medical device as in claim 6, wherein said data compression device divides the time interval between heart beats into said plurality of sub-ranges, and said data compression devices uses said resolution value to obtain the digital encoded signal for measured heart beat intervals based upon the sub-range that the heart beat interval falls within.

9. An implantable medical device as in claim 8, wherein the plurality of sub-ranges includes a first sub-range, a second sub-range, a third sub-range, and a fourth sub-range.

10. An implantable medical device as in claim 9, wherein the resolution applied in the first sub-range is approximately 10 milliseconds.

11. An implantable medical device as in claim 10, wherein the resolution applied in the second sub-range is approximately 20 milliseconds.

12. An implantable medical device as in claim 11, wherein the resolution applied in the third sub-range is approximately 40 milliseconds.

13. An implantable medical device as in claim 12, wherein the resolution applied in the fourth sub-range is approximately 80 milliseconds.

14. An implantable medical device as in claim 9, wherein the first sub-range comprises heart beat intervals between approximately 170 milliseconds and approximately 425 milliseconds.

15. An implantable medical device as in claim 14, wherein the second sub-range comprises heart beat intervals between approximately 425 milliseconds and approximately 725 milliseconds.

16. An implantable medical device as in claim 15, wherein the third sub-range comprises heart beat intervals between approximately 725 milliseconds and approximately 1350 milliseconds.

17. An implantable medical device as in claim 16, wherein the fourth sub-range comprises heart beat intervals between approximately 1350 milliseconds and approximately 2000 milliseconds.

18. An implantable medical device as in claim 1, wherein said sensor comprises an accelerometer and said physiological parameter comprises acceleration values.

19. An implantable medical device as in claim 1, wherein said sensor comprises a temperature sensor and said physiological parameter comprises temperature values.

20. An implantable medical device as in claim 1, wherein said sensor comprises a blood pressure sensor and physiological parameter comprises blood pressure values.

21. An implantable medical device as in claim 1, wherein said sensor comprises a pulse oximetry sensor and said physiological parameter comprises blood oxygen saturation levels.

22. An implantable medical device as in claim 1, wherein the status information stored together with the digital encoded signal comprises physiological status information.

23. A method for compressing electrical signals representing a physiological parameter into a digital encoded value with a predetermined number of bits n, comprising the steps of:
  measuring the physiological parameter and providing an output signal indicative thereof;
  compressing the output signal to obtain a compressed encoded value, wherein the step of compressing includes:
    sub-dividing the possible values of the output signal into sub-ranges ranging from a lowest expected value to a highest expected value;
    assigning a resolution value for each of the sub-ranges to maintain a maximum error value for the compression;
    calculating the digital encoded value for the output signal based upon the particular sub-range in which the output signal falls within, and the resolution assigned to that sub-range.

24. A method as in claim 23, wherein the output signal comprises a digital signal with a bit width z.

25. A method as in claim 24, wherein the bit width n of the encoded signal is six or less.

26. A method as in claim 24, wherein the bit width z is greater than eight, and the bit width n of the encoded signal is less than eight.

27. A method as in claim 23, wherein the physiological parameter is the interval between heart beats.

28. A method as in claim 27, wherein the lowest expected value is approximately 170 milliseconds, and the highest expected value is approximately 2600 milliseconds.

29. A method as in claim 28, wherein the sub-ranges include a first range between approximately 170 milliseconds and approximately 425 milliseconds.

30. A method as in claim 29, wherein the sub-ranges include a second sub-range between approximately 425 milliseconds and approximately 725 milliseconds.

31. A method as in claim 30, wherein the sub-ranges include a third sub-range between approximately 725 milliseconds and approximately 1350 milliseconds.

32. A method as in claim 31, wherein the sub-ranges include a fourth sub-range between approximately 1350 milliseconds and approximately 2000 milliseconds.

33. A method as in claim 32, wherein the resolution assigned to the first sub-range is approximately 10 milliseconds.

34. A method as in claim 33, wherein the resolution assigned to the second sub-range is approximately 20 milliseconds.

35. A method as in claim 34, wherein the resolution assigned to the third sub-range is approximately 40 milliseconds.

36. A method as in claim 35, wherein the resolution assigned to the fourth sub-range is approximately 80 milliseconds.

37. A method for compressing electrical signals representing physiological parameters into a digital encoded value with a predetermined number of bits n, comprising the steps of:
  sub-dividing the possible values of the electrical signal into a plurality of sub-ranges, with each sub-range having a start interval value and an end interval value, and a corresponding start encoded value and an end encoded value;
  assigning a resolution value for each of the plurality of sub-ranges to maintain a maximum error value for the compression;
  calculating the digital encoded value for the electrical signal by;
    determining the sub-range that the electrical signal falls within;
    subtracting the start interval value for that range from the electrical signal;
    dividing the difference by the resolution value assigned that range to obtain a relative encoded value;
    adding the start encoded value to the relative encoded value to obtain the digital encoded value;
    storing the digital encoded value in memory.

38. A method as in claim 37, wherein the maximum error value is less than approximately 6.0%.

39. A method for compressing digital signals representing physiological parameters into a digital encoded value with a predetermined number of bits n, comprising the steps of:

sub-dividing the possible values of the digital signal into at least two sub-ranges, with each sub-range having a start interval value and an end interval value, and a corresponding start encoded value and an end encoded value;

assigning a resolution value for each of the sub-ranges to maintain a maximum error value for the compression;

calculating the digital encoded value for the digital signal by;
 dividing the digital signal by the resolution value of the first sub-range to obtain a quotient;
 dividing the start interval value for the first range by the resolution value of the first range to obtain an offset value;
 subtracting the offset value from the quotient to obtain a first estimated digital encoded value;
 comparing said estimated digital code value with the start encoded value for said second sub-range, and selecting said estimated digital code value as the digital encoded value for said digital signal if said first estimated digital code value is less than the start encoded value of the second sub-range.

40. A method as in claim 39, wherein the first estimated digital code value is corrected if said estimated code value is equal to or greater than the start encoded value of the second sub-range.

41. A method as in claim 40, wherein the estimated code value is corrected by subtracting the start encoded value for the second sub-range from the first estimated digital code value, dividing the difference by two to obtain a corrected quotient, and adding the start encoded value for the second sub-range to the corrected quotient to obtain a second estimated digital code value.

42. A method as in claim 39, wherein the possible values of the digital signal are sub-divided into at least three sub-ranges, with each sub-range having a start interval value and an end interval value, and a corresponding start encoded value and an end encoded value.

43. A method as in claim 42, wherein the possible values of the digital signal are sub-divided into at least four sub-ranges, with each sub-range having a start interval value and an end interval value, and a corresponding start encoded value and an end encoded value.

44. An implantable medical device for sensing a physiological parameter and storing encoded signals indicative of the sensed physiological parameter, comprising:
 a sensor for sensing the physiological parameter and providing an output signal indicative of said physiological parameter;
 a signal processing device for receiving the output signal from said sensor and providing a digital signal representing the sensed physiological parameter;
 a data compression device for compressing the distal signal into a digital encoded signal with a predetermined bit width n, wherein the data compression device divides the digital signal from said signal processing device into a plurality of sub-ranges, and applies a different resolution value to each sub-range during compression; and
 a memory device for storing said digital encoded signal.

* * * * *